United States Patent
Cooper et al.

(10) Patent No.: US 6,449,932 B1
(45) Date of Patent: Sep. 17, 2002

(54) OPTOELECTRONIC APPARATUS FOR DETECTING DAMAGED GRAIN

(75) Inventors: William F. Cooper, Hawley, MN (US); Karl-Heinz O. Mertins, Fargo, ND (US); Timothy Schaefer, Los Alamos, NM (US)

(73) Assignee: Deere & Company, Moline, IL (US)

( * ) Notice: Subject to any disclaimer, the term of this patent is extended or adjusted under 35 U.S.C. 154(b) by 0 days.

(21) Appl. No.: 09/720,528
(22) PCT Filed: Jun. 29, 1999
(86) PCT No.: PCT/US99/14436
§ 371 (c)(1), (2), (4) Date: Apr. 2, 2001
(87) PCT Pub. No.: WO00/00818
PCT Pub. Date: Jan. 6, 2000

Related U.S. Application Data
(60) Provisional application No. 60/091,061, filed on Jun. 29, 1998.

(51) Int. Cl.$^7$ .................................................. A01D 46/28
(52) U.S. Cl. ..................................................... 56/10.2 R
(58) Field of Search ........................ 56/10.2 R, 10.2 A, 56/10.2 C, 10.2 J, 10.2 G; 460/7, 6, 1, 4; 356/328, 339.1; 250/339.09; 209/588

(56) References Cited

U.S. PATENT DOCUMENTS

| | | | | |
|---|---|---|---|---|
| 4,077,774 A | * | 3/1978 | Neti et al. | 23/232 R |
| 4,348,855 A | * | 9/1982 | DePauw et al. | 56/10.2 R |
| 4,421,772 A | * | 12/1983 | Munck et al. | 426/231 |
| 4,572,666 A | * | 2/1986 | Satake | 356/239 |
| 5,132,538 A | * | 7/1992 | Norris | 250/339 |
| 5,751,421 A | * | 5/1998 | Wright et al. | 356/328 |

FOREIGN PATENT DOCUMENTS

| | | | | |
|---|---|---|---|---|
| EP | 0 826 959 A1 | * | 3/1998 | G01N/21/88 |
| EP | 0 841 557 A2 | * | 5/1998 | G01N/21/64 |

* cited by examiner

*Primary Examiner*—Robert E. Pezzuto

(57) ABSTRACT

An optoelectronic apparatus having a measurement region (38) for detecting the presence of damaged or cracked grain kernels in a population of grain kernels which are either in a stationary or moving state at the measurement region. The apparatus comprises a short-wave ultraviolet excitation light source (20) that emits a spectral line of a wavelength shorter than 300 nm, a non-imaging photon detector (22), and wavelength selector such as a dichroic beam-splitter (28) which serves to isolate the fluorescent light emitted in a certain spectral region by the endosperm of grain from the excitation light of the light source, as well as from other sources of light. The apparatus may be mounted in a combine harvester for the purpose of detecting the presence of damaged grain kernels that have endosperm exposed while harvesting.

17 Claims, 5 Drawing Sheets

OPTOELECTRONIC APPARATUS FOR DETECTING DAMAGED GRAIN

This application is a 371 of PCT/US99/14436 filed Jun. 29, 1999, which claims benefit of provisional application No. 60/091,061, filed Jun. 29, 1998.

TECHNICAL FIELD

The invention is directed to a combine with a novel short-wave U.V. excited, (herein, short-wave U.V. is defined as U.V. light having a wavelength of 300 nm or less) fluorescence sensor used to detect levels of damage in grains or seeds, including but not limited to cracked or broken conditions in the grain or biological contamination. This sensor can be used on grain that is in either a stationary or a moving state, and therefore is used in an operating combine harvester (hereinafter combine), for example in a grain elevator for quality control. Hereinafter, the sensor will be referred to as either a cracked grain sensor or simply a sensor.

BACKGROUND ART

The prior art suggests the desirability of having an effective method for detecting grain which has been mechanically damaged, or cracked. Many of the methods which have been hitherto developed are only usable in a laboratory setting, and are not adaptable to real-time use in a combine.

Some methods require that a chemical solution be applied to the grain (U.S. Pat. Nos. 4,000,975 and 4,020,682), which can render such grain harmful for human or animal consumption. Other methods require undue destructive sample preparation (U.S. Pat. No. 4,000,975), which precludes the use of those methods for real-time detection of damaged grain kernels in a continuous flow of grain material.

U.S. Pat. No. 4,572,666 discloses a through-beam method for the detection of cracked rice, in which a coherent light beam is passed through individual rice grains. Such a method is limited to grain of a translucent nature and can only be used with small quantities of grain, such as in a laboratory setting.

U.S. Pat. No. 4,348,855 proposes an arrangement of sieves and impact transducers (similar to those used for grain loss monitoring) to separate and detect damaged grain inside a combine. However, this method does not adequately discriminate between small but intact grain kernels versus pieces of debris and broken pieces of larger grain kernels.

Infrared and near-infrared methods such as described in U.S. Pat. Nos. 5,132,538, 4,806,764, and 5,751,421 are used primarily to determine the constituents of grain, such as oil, protein, starch, and moisture and are not intended for damage detection. Likewise, U.S. Pat. No. 4,421,772, which uses a range of visible, ultraviolet and/or X-ray radiation to determine characteristic fluorescence from the component parts of ground seeds and other botanical matter, is not targeted for grain damage detection. However, this patent teaches the use of short-wave UV as an optimum excitation wavelength for the detection of fluorescence emission related to the starchy endosperm of grains.

Other methods use either machine vision under visible light (see "Image Processing and Neural Networks Classify Complex Defects" by Wilson, in Vision Systems Design, March, 1999) or machine vision augmented with long-wave UV light (U.S. Pat. No. 4,713,781) Machine vision requires expensive imaging components, such as CCD cameras, artificial illumination, and complex signal processing means. Despite progress in the performance of machine vision systems, the complexity of the task does not allow for processing speeds essential to real-time applications. Also, the use of a CCD camera dictates the selection of long-wave UV excitation, rather than the more effective short-wave UV excitation, thereby impairing the capability of accurately determining the presence of damaged grain, because more background light from the source reaches the detector.

DISCLOSURE OF THE INVENTION

A first object of the present invention is to provide an apparatus for detecting levels of damage in grains or seeds, including but not limited to cracked or broken conditions in the grain. A second object of the present invention is to provide a short-wave U.V. excited fluorescence sensor which will detect levels of damage in grains or seeds in a fast, accurate, and consistent manner. A third object of the present invention is to provide a damaged grain sensor applicable to grain that is in either a stationary or a moving state, and therefore the sensor can be used in an operating combine, in a grain elevator for quality control, or as a hand held detecting device.

These and other objectives are achieved by the present invention, which includes an ultraviolet light source that provides a certain short-wave UV excitation wavelength (e.g., 253.6 nm) to which the grain is exposed. Different constituents of grain emit different levels of fluorescence. The endosperm of grain, when exposed to said certain excitation wavelength will fluoresce at a certain emission wavelength (e.g., 335 nm) with a substantially higher intensity than will the pericarp, or hull of the grain. Therefore, if grain has been damaged, such that the grain has been cracked or broken so as to expose the endosperm, a measurable difference in fluorescence intensity can be detected between the damaged and undamaged states of the grain by using a non-imaging photon detector. Other elements of the invention are present in order to concentrate the desired fluorescence signal on the non-imaging photon detector and to process the signal from the photon detector.

The present invention is advantageous as compared to the prior art in that the sample is not exposed to chemicals. Nor is undue preparation of the sample or destruction of the sample required. The present invention can be used with a wide variety of grain types and is not reliant upon through-beam illumination, which is unsuitable for high volume flow as well as for measuring damage to grains that are not translucent. Because the present invention does not rely on imaging of the sample onto the detector, optical components that may be used to gather light in order to concentrate the luminescence onto the detector can be inexpensive. Further, the complexity of signal processing is drastically reduced and the signal processing time is shortened so that real-time measurement applications are feasible. Additionally, the present invention allows the use of more effective, short-wave UV radiation for fluorescence excitation, which minimizes the detection of false signals. For the above reasons the apparatus of the present invention may be built of standard electronic and optical components that are available at low cost.

BRIEF DESCRIPTION OF THE DRAWINGS

The present invention will become more fully understood from the detailed description given below and the accompanying drawings, which are given by way of illustration only and thus are not limitative of the present invention, wherein.

BEST MODE FOR CARRYING OUT THE INVENTION

The following description of the preferred embodiments directed to a damaged grain sensor is merely exemplary in nature and is in no way intended to limit the invention or its applications or uses. For simplification, discussion of the damaged grain will be directed to cracked or broken grain within a combine. The data obtained from the damaged grain sensor(s) can be displayed to the combine operator, who can adjust grain separation and grain cleaning devices in a manner so that a predefined level of grain quality is maintained. Alternatively, the data from the damaged grain sensor(s) can be fed into a closed loop control system to allow automatic adjustment of the combine settings.

It has been established that, when exposed to a certain UV excitation wavelength (e.g., 253.6 nm), different constituents of grain emit different levels of fluorescence. The endosperm of grain, when exposed to this excitation wavelength, will fluoresce at a certain emission wavelength (e.g., 335 nm) with a substantially higher intensity than will the pericarp, or hull of the grain. Therefore, if grain has been damaged to the extent of being cracked or broken so as to expose the endosperm, a measurable difference in fluorescence intensity can be detected between the damaged and undamaged states of the grain.

It is to be understood that parts of the grain other than the endosperm can be targeted (e.g., the aleurone), by using different excitation wavelengths and monitoring different emission wavelengths, thereby targeting a different part of the damaged grain kernel.

Figure 1:
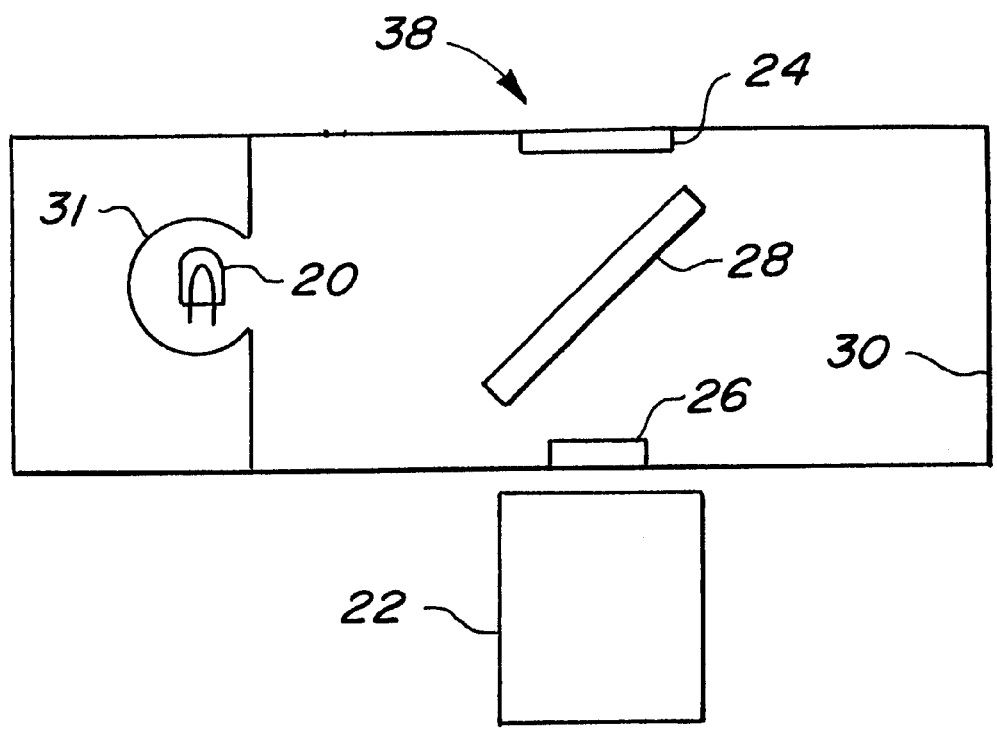
FIG. 1 shows the component configuration of a first embodiment of the sensor of the present invention.

FIG. 1 is a diagram illustrating an embodiment of the component configuration of the sensor. The embodiment of the invention depicted in FIG. 1 is configured to be used as a cracked or broken grain sensor in an operating combine, in a grain elevator for quality control, or as a hand held detecting device. In the application as a sensor for detecting cracked or broken grain, a certain UV excitation wavelength is emitted (e.g., 253.6 nm) and a certain UV emission wavelength is monitored (e.g., 335 nm).

It is to be understood that other embodiments of the invention (not illustrated) may target (i.e., include) the detection of other types of grain damage, such as biological contamination (e.g., mold, mildew, or insects), and can require the use of one or more different UV excitation wavelengths and the monitoring of one or more different UV emission wavelengths. Embodiments for such applications may require other configurations, which would include multiple components of differing parameters (e.g., two or more detectors for different wavelengths). Also, the collection of additional photonic information (e.g., detection of reflected light for mass flow extrapolation) may require the addition of components that might require a change in the sensor configuration.

Information from other existing sensors that are part of a modem combine (e.g., clean grain yield or mass flow sensor, tailings sensor, grain moisture sensor) can also be used in conjunction with the damaged grain sensor. This is commonly referred to as a fused sensor concept and can further enhance the usefulness of the damaged grain sensor.

A light source 20, preferably consisting of an uncoated low-pressure UV mercury lamp, supplies the excitation wavelength(s) for the sensor. A photon detector 22, which can be a photo multiplier tube (PMT) or a silicon detector especially designed for the detection of short-wave UV (e.g., Siemens ultraviolet selective sensor SFH 530), is used as the sensor detector.

A sensor window 24 is provided adjacent a measurement region 38 to separate the optoelectronic components of the sensor from grain (not illustrated) located at the measurement region. The sensor window 24 is preferably made of sapphire because of its ability to pass UV radiation and its durability and scratch resistance. In certain applications (e.g., hand held devices) where abrasion is not a concern, less expensive quartz may be used for the sensor window 24. On a combine, however, the abrasion caused by debris and sand moving rapidly across the window would quickly frost up quartz and, therefore, sapphire is recommended for such an operating environment.

A filter 26 may be provided as a wavelength selector. In one embodiment the filter 26 is a bandpass filter centered at 335 nm with a bandpass of 20 nm (335 nm coincides with the wavelength of maximum intensity of the fluorescence for endosperm of grain excited with light at 253.6 nm wavelength). An inherent disadvantage of such a filter is that the transmission efficiency even at its nominal pass wavelength is typically only 30 percent. Thus, most of the fluorescence that is generated by the grain is lost. In other embodiments, the filter 26 can be changed to accept different wavelength ranges.

A sensor sensitive in different wavelength ranges could be substituted in order to enhance the photon detecting capability for solid state photon detection or to target the UV sensor for the detection of specific grain damage, such as the presence of biological contaminants or cracks in the grain kernel. Two reasons to vary the parameters of the filter 26 would be: to increase the fluorescence signal throughput, so that a solid state photon detector can be used; and to enable an estimate of the actual mass flow of grain passing by the sensor window 24 by monitoring sensor signal fluctuations due to the fluorescence of the pericarp of the grain. Mass flow estimates can also be obtained from another sensor within the combine, e.g., a clean grain yield sensor (not shown). In some embodiments (not illustrated), filter 26 may be eliminated, due to the wavelength selective capabilities of the dichroic beam splitter 28 and the fact that certain photon detectors 22 having filters that are formed integrally with the photon detector.

In the preferred embodiment, a dichroic beam-splitter 28 is used as the wavelength selector to isolate the excitation wavelength (e.g., 253.6 nm) emitted by the light source 20 from as much of the longer fluorescence output wavelengths as possible. The dichroic beam-splitter 28, in this embodiment, is a 288 nm long-pass filter. Substantially all the light from the light source 20 of a wavelength shorter than 288 nm is reflected toward the sensor window 24. The light having wavelengths that are longer than approximately 300 nm is transmitted with about 85–90 percent efficiency through the beam-splitter and into a beam dump 30.

The dichroic beam-splitter 28 also filters UV radiation emitted from the exposed endosperm of the grain that is present at the measurement region 38 on the outer side of the sensor window 24. The dichroic beam-splitter 28 filters in such a way that light emissions and scattered/reflected light shorter than 288 nm are reflected and any light emissions and scattered light longer in wavelength than approximately 300 nm are allowed to pass through. The light emissions of interest from the endosperm are of wavelengths longer than 300 nm, so it passes through the dichroic beam-splitter 28 to the bandpass filter 26 and to the photon detector 22. In the described embodiment, the dichroic beam-splitter 28 is manufactured to operate at a 45 degree angle with respect to the incident radiation.

The entire interior, excluding the light source cavity 31, is covered with a light absorbing material, such as black paint or other surface treatment, and acts as a beam dump 30 to absorb unwanted light.

Figure 2:
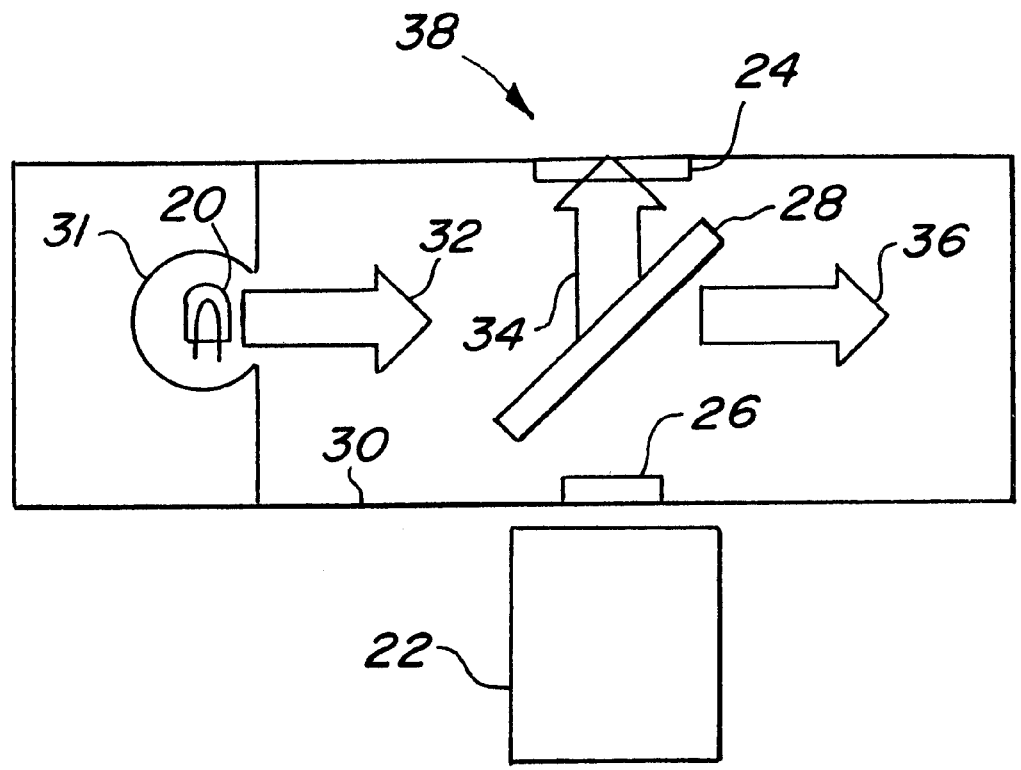
FIG. 2 illustrates the excitation light as it is separated into two wavelength components by a dichroic beam-splitter.

FIG. 2 illustrates the excitation light as it is separated into two wavelength components by a dichroic beam-splitter. Light 32 from the light source 20 is incident on the dichroic beam-splitter 28 at a substantially 45 degree angle, with respect to the plane of the filter 26. Light 32 from the light source 20 includes all wavelengths output by the light source 20. Light 32 is incident on the dichroic beam-splitter 28 and is separated into a short wavelength constituent 34 and a long wavelength constituent 36. The short wavelength constituent 34 includes the predominant 254 nm emission line radiation from the light source 20 and is reflected toward the sensor window 24. The long wavelength constituent 36, in this embodiment, includes all radiation greater than approximately 300 nm, which is transmitted through the dichroic beam splitter 28 and is absorbed in the beam dump 30.

Figure 3:
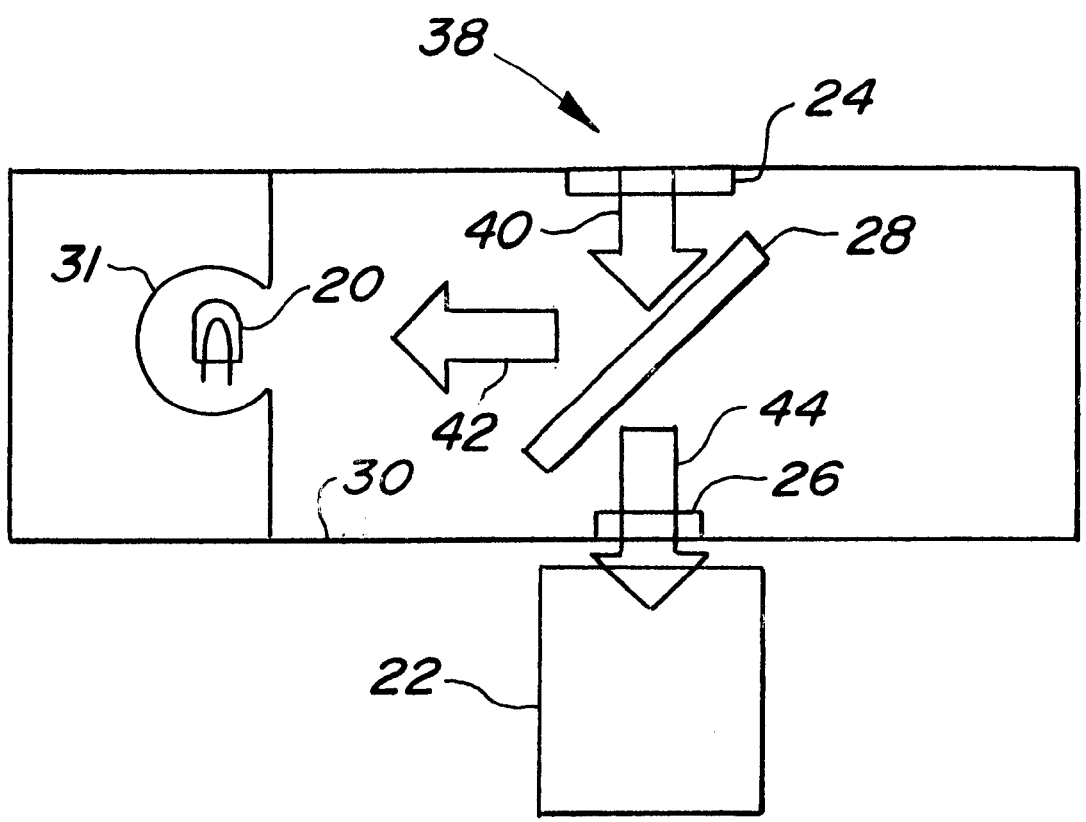
FIG. 3 illustrates the combined fluorescence emission and scattered/reflected excitation light as it is separated into two wavelength components by the dichroic beam-splitter.

FIG. 3 illustrates the fluorescence and scattered/reflected excitation light as it is separated into two wavelength components by the dichroic beam-splitter 28. Light 40, which passes through the sensor window 24, consists of scattered light from the light source 20, including reflected light from short wavelength constituent 34 (FIG. 2), and fluorescent light emitted from grain located at measurement region 38. The light 40 is incident on the dichroic beam splitter 28 and is separated into a short wavelength constituent 42 and a long wavelength constituent 44. Short wavelength constituent 42 consists of wavelengths of 288 nm and shorter, including the 253.6 nm wavelength radiated from the light source 20. The short wavelength constituent 42 is reflected from the mirrored surface of the dichroic beam splitter 28 and is absorbed in the beam dump 30. The long wavelength constituent 44 consists of wavelengths of 300 nm and longer, including the fluorescence emission wavelengths (i.e., near 335 nm) from grain located at measurement region 38. This long wavelength constituent is then incident on the filter 26.

Figure 4:
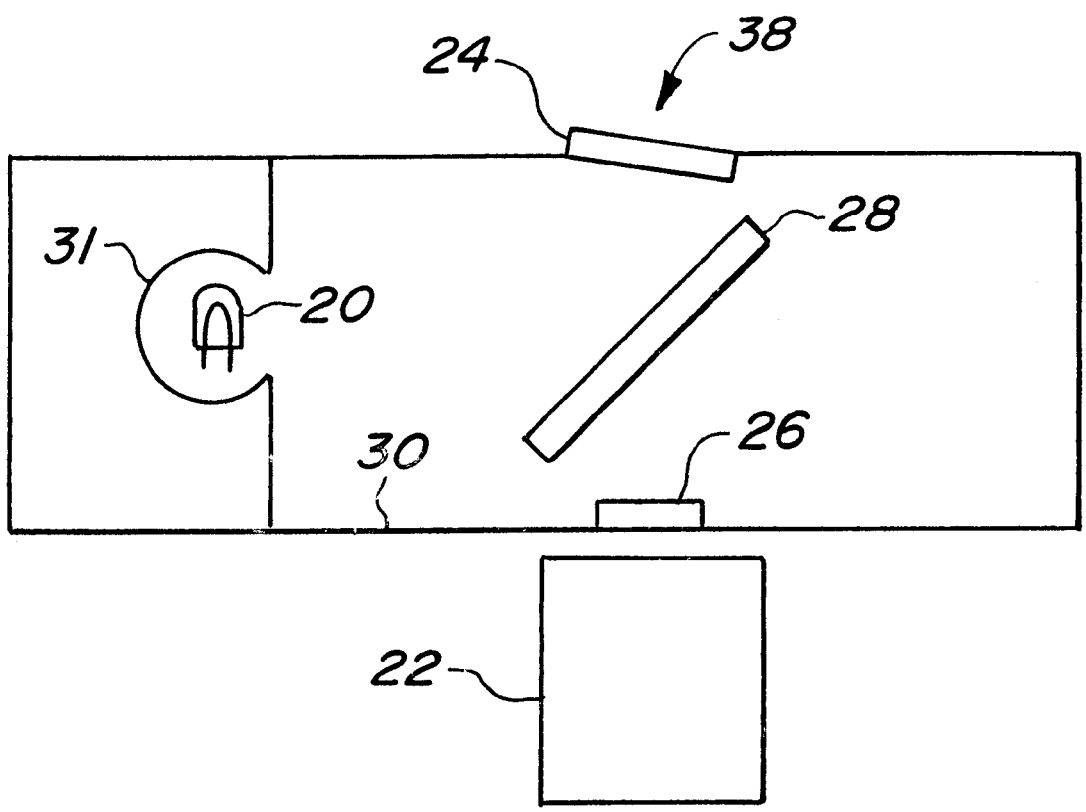
FIG. 4 shows the component configuration of a second embodiment of the sensor of the present invention, wherein there is provided an alternative sensor window configuration.

FIG. 4 is a diagram which shows the component configuration of a second embodiment of the apparatus of the present invention, wherein there is provided an alternative sensor window configuration. In the previous embodiments, the sensor window 24 is parallel to the filter 26 surface. In order to reduce the back-scatter from the light source 20, an embodiment in which the sensor window 24 is angled and physically reflects the back-scatter away from the photon detector 22 is devised. The embodiment illustrated in FIG. 4 depicts the sensor window 24 tilted at a small angle (e.g., 5–10 degrees) with respect to the plane defined by the filter 26, and in a direction such that the angle between the surface of the dichroic beam-splitter 28 and the surface of the window 24 is greater than 45 degrees.

In another embodiment (not shown), the sensor window 24 of the sensor is tilted at an angle of 5–45 degrees with respect to the plane defined by the filter 26, and in a direction such that the angle between the surface of the dichroic beam-splitter 28 and the surface of the window 24 is less than 45 degrees.

Figure 5:
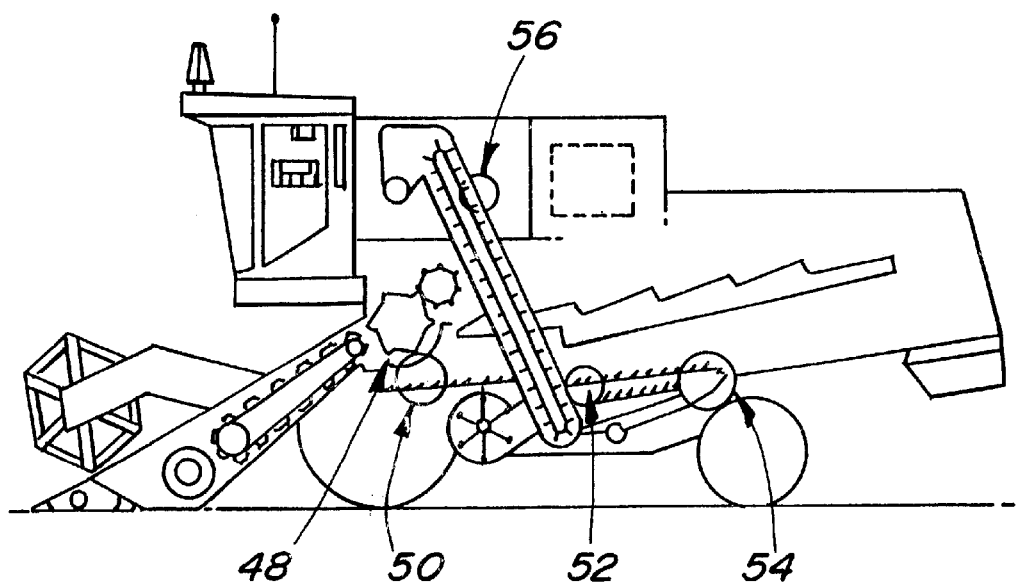
FIG. 5 shows the areas on a combine which have been identified for possible placement of the cracked grain sensor.

FIG. 5 is a drawing of a combine on which areas have been identified for possible placement of the cracked grain sensor. These areas include, but are not limited to, the grain conveyance area 50 that is located directly under the concave 48, the chaffer/sieve area 52, the exit from the cleaning shoe 54, and the dean grain elevator 56. Placing the sensor in the grain shuttle area 50 will yield information on the actual amount of cracked grain that is being generated in the threshing process. This information can be used to indicate changes in the threshing efficiency during harvest, if used as a relative measurement In conjunction with mass flow or yield measurements, information from the grain shuttle area 50 will indicate the actual percentage of grain being damaged in the threshing process. Data gathered from the chaffer/sieve area 52 indicates how much of the grain being cracked is small enough to be excluded from the dean grain system. If placed at the exit of the cleaning shoe 54, the data will indicate the relative amount of cracked grain that is being expelled from the combine. Data gathered from the dean grain system 56 will yield information on the percentage of cracked grain that will be delivered to the market. The cracked grain sensor can also be placed in the grain conveyance mechanism that is underneath the threshing mechanism or in the dean grain elevator or in the clean grain unloading system of the combine harvester. Use of two or more damaged grain sensors in different places on the combine will give a good indication of the overall efficiency of the combining process.

INDUSTRIAL APPLICABILITY

As discussed above, the invention has uses as a damaged grain sensor for grain that is in either a stationary or a moving state, and therefore the sensor can be used in an operating combine, in a grain elevator for quality control, or as a hand held detecting device.

The invention being thus described, it will be obvious that the same may be varied in many ways. For example, a lens or reflector may be used to concentrate the fluorescent radiation onto a detecting surface of the non-imaging photon detecting device. Such lens or reflector may be made integral with the non-imaging photon detecting device or may be a separate component. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. A combine harvester comprising means for harvesting crop, means for separating grain kernels from the harvested crop, and a detection apparatus for detecting damaged grain kernels among the grain kernels, the detection apparatus including an ultraviolet light source (20) having an emission line at a wavelength shorter than 300 nm, a measurement region (38) in which said grain kernels which are either in a stationary or a moving state are located, a wavelength selector, a non-imaging photon detecting device (22), wherein, when said apparatus is in use, light from the ultraviolet light source (20) irradiates grain kernels positioned at the measurement region (38), the wavelength selector and the photon detecting device (22) are arranged such that light which is emitted in the measurement region (38) passes the wavelength selector and falls onto the photon detecting device (22), whereby the wavelength selector substantially prevents light having wavelengths shorter than 300 nm from being incident onto the non-imaging photon detecting device, such that provided that a grain kernel in the measurement region (38) is damaged to the extent that the endosperm of the kernel is exposed, more fluorescence emission from the damaged grain kernel in the wavelength from 300 nm to 380 nm is incident on and detected by the photon detecting device (22) than when the kernel is not damaged.

2. The combine harvester of claim 1 wherein the ultraviolet light source (20) has an emission line at about 253.6 nm wavelength.

3. The combine harvester of claim 1 wherein the wavelength selector includes a filter (26) that allows wavelengths in the range from 300 nm to 380 nm to be incident on said non-imaging photon detecting device (22) and that substantially prevents light with wavelengths shorter than 300 nm from being incident on said photon detecting device (22).

4. The combine harvester of claim 1 wherein the wavelength selector includes a beam-splitter (28) which separates a desired excitation wavelength from other wavelengths radiated by said ultraviolet light source (20) and directs said desired excitation wavelength to the measurement region (38), said beam splitter (38) also serving to pass a fluorescence emission at a specified wavelength which occurs at the measurement region (38) so as to be incident onto said photon detecting device (22) while substantially preventing light with wavelengths shorter than 300 nm from being incident on said photon detecting device (22).

5. The combine harvester of claim 1 wherein non-imaging photon detecting device (22) is a photo multiplier tube.

6. The combine harvester of claim 1 wherein the non-imaging photon detecting device (22) is a silicon-based detector.

7. The combine harvester of claim 6 wherein the wavelength selector is a filter that is integral with the silicon-based detector (22).

8. The combine harvester of claim 1 wherein the detection apparatus further includes a housing in which the ultraviolet light source (20) and the photon detecting device (22) are located, the housing having a window (24) formed of sapphire or quartz through which the light from said ultraviolet light source (20) can irradiate grain kernels positioned at the measurement region (38) and which allows fluorescence emission from a damaged grain kernel to enter the housing so as to be directed to said photon detecting device (22).

9. The combine harvester of claim 8 further comprising a light absorbing substance on an interior surface of the housing which thereby serves as a beam dump (30).

10. The combine harvester of claim 8 wherein the window (24) encloses a non-perpendicular angle with the axis of the incident beam provided by the ultraviolet light source (20), in order to reduce back-scatter from the light source (20) incident on the photon detector (22).

11. The combine of claim 1 further comprising a threshing mechanism and a grain conveyance area (50) mounted underneath the threshing mechanism and wherein the detection apparatus is mounted in the grain conveying area (50).

12. The combine harvester of claim 1 further comprising a clean grain elevator and wherein the detection apparatus is mounted in the clean grain elevator.

13. The combine harvester of claim 1 further comprising a clean grain storage tank and wherein the detection apparatus is mounted in the clean grain storage tank.

14. The combine harvester of claim 1 further comprising a clean grain unloading system and wherein the detection apparatus is mounted in the clean grain unloading system.

15. The combine harvester of claim 1 further comprising a grain separation mechanism and wherein the detection apparatus is mounted in the grain separation system.

16. A method for detecting damaged grain kernels during operation of a combine harvester, comprising the steps of:
(a) irradiating grain kernels at a measurement region (38) of said combine harvester using ultraviolet light having an emission line at a wavelength shorter than 300 nm; and
(b) with a non-imaging photon detector (22), detecting light from said measurement region (38) having wavelengths longer than 300 nm, while substantially preventing light having wavelengths shorter than 300 nm from being detected by said non-imaging photon detector (22).

17. A method for detecting damaged grain kernels among a sample of grain kernels comprising the steps of:
providing an ultraviolet light source (20) having an emission line at a wavelength shorter than 300 nm, a non-imaging photon detecting device (22), and a wavelength selector which substantially prevents light having wavelengths shorter than 300 nm from passing therethrough arranged such that when the ultraviolet light source (20) is in use, light from the ultraviolet light source (20) irradiates grain kernels positioned at a measurement region (38) and light which is emitted in the measurement region (38) having a wavelength greater than 300 nm passes the wavelength selector and falls onto the photon detecting device (22) whereby when grain damaged to the extent that the endosperm of the kernel is exposed, fluorescence emission from the damaged grain kernel in the wavelength from 300 nm to 380 nm is incident on and detected by the photon detecting device (22);
irradiating grain kernels at the measurement region (38) using the ultraviolet light source (20), and
determining the extent of damaged grain kernels by the fluorescence emission from the measurement region (38) detected by the photon detecting device (22).

\* \* \* \* \*